United States Patent
Stratton

(10) Patent No.: US 12,233,200 B2
(45) Date of Patent: *Feb. 25, 2025

(54) CARTRIDGES FOR VAPORIZER DEVICES

(71) Applicant: JUUL Labs, Inc., San Francisco, CA (US)

(72) Inventor: Andrew J. Stratton, Royston (GB)

(73) Assignee: JUUL Labs, Inc., Washington, DC (US)

( * ) Notice: Subject to any disclaimer, the term of this patent is extended or adjusted under 35 U.S.C. 154(b) by 361 days.

This patent is subject to a terminal disclaimer.

(21) Appl. No.: 17/861,314

(22) Filed: Jul. 11, 2022

(65) Prior Publication Data
US 2023/0001109 A1   Jan. 5, 2023

Related U.S. Application Data

(63) Continuation of application No. 16/674,762, filed on Nov. 5, 2019, now Pat. No. 11,383,049.
(Continued)

(51) Int. Cl.
*A61M 11/04* (2006.01)

(52) U.S. Cl.
CPC ... *A61M 11/042* (2014.02); *A61M 2205/0272* (2013.01); *A61M 2205/3331* (2013.01)

(58) Field of Classification Search
CPC ........ A24F 40/10; A24F 40/42; A24F 40/465; A24F 40/46; A24F 40/485; A24F 40/48; A24F 40/30
See application file for complete search history.

(56) References Cited

U.S. PATENT DOCUMENTS

| | | |
|---|---|---|
| 6,889,687 B1 | 5/2005 | Olsson |
| 7,766,013 B2 | 8/2010 | Wensley et al. |
| (Continued) | | |

FOREIGN PATENT DOCUMENTS

| | | |
|---|---|---|
| CN | 203952435 U | 11/2014 |
| CN | 107429635 A | 12/2017 |
| (Continued) | | |

OTHER PUBLICATIONS

U.S. Appl. No. 16/674,762, filed Nov. 5, 2019, U.S. Pat. No. 11,383,049.
(Continued)

*Primary Examiner* — Truc T Nguyen
(74) *Attorney, Agent, or Firm* — Mintz, Levin, Cohn, Ferris, Glovsky and Popeo, P.C.

(57) ABSTRACT

Cartridges for vaporizer devices are provided. In one exemplary embodiment, the cartridge can include first and second storage chambers each configured to hold a respective fraction of a vaporizable material, a vaporization chamber that includes an elongate member that is in fluid communication with the first and second storage chambers and configured to receive the vaporizable material, a magnetic element disposed within a channel of the elongate member, and a conductive element that is configured to generate a first motive force to drive the magnetic element between first and second positions and further configured to substantially vaporize the vaporizable material within the elongate member. Vaporizer devices are also provided.

20 Claims, 4 Drawing Sheets

Related U.S. Application Data

(60) Provisional application No. 62/755,965, filed on Nov. 5, 2018.

(56) References Cited

U.S. PATENT DOCUMENTS

| | | | |
|---|---|---|---|
| 8,434,478 | B2 | 5/2013 | Yamada et al. |
| 8,464,867 | B2 | 6/2013 | Holloway et al. |
| 8,961,492 | B2 | 2/2015 | Imran et al. |
| 8,975,764 | B1 | 3/2015 | Abehasera |
| 9,332,787 | B2 | 5/2016 | Liu |
| 9,345,541 | B2 | 5/2016 | Greeley et al. |
| 9,763,478 | B2 | 9/2017 | Cameron et al. |
| 9,770,055 | B2 | 9/2017 | Cameron et al. |
| 9,808,071 | B2 | 11/2017 | Thiebaut et al. |
| 9,844,234 | B2 | 12/2017 | Thorens et al. |
| 9,888,723 | B2 | 2/2018 | Cameron et al. |
| 10,058,128 | B2 | 8/2018 | Cameron et al. |
| 10,058,129 | B2 | 8/2018 | Monsees et al. |
| 10,085,481 | B2 | 10/2018 | Verleur et al. |
| 10,085,486 | B2 | 10/2018 | Cameron |
| 10,130,119 | B2 | 11/2018 | Murison |
| 10,131,532 | B2 | 11/2018 | Murison et al. |
| 10,193,364 | B2 | 1/2019 | Xiang |
| 10,194,693 | B2 | 2/2019 | Wensley et al. |
| 10,272,170 | B2 | 4/2019 | Dubief |
| 10,292,427 | B2 | 5/2019 | Cameron et al. |
| 11,383,049 | B2 * | 7/2022 | Stratton .............. A61M 11/042 |
| 2002/0142291 | A1 | 10/2002 | Bauer et al. |
| 2003/0015045 | A1 | 1/2003 | Yoshida et al. |
| 2005/0022806 | A1 | 2/2005 | Beaumont et al. |
| 2005/0268909 | A1 | 12/2005 | Bonney et al. |
| 2006/0196518 | A1 | 9/2006 | Hon |
| 2008/0038363 | A1 | 2/2008 | Zaffaroni et al. |
| 2010/0181387 | A1 | 7/2010 | Zaffaroni et al. |
| 2011/0036363 | A1 | 2/2011 | Urtsev et al. |
| 2012/0230659 | A1 | 9/2012 | Goodman et al. |
| 2012/0261286 | A1 | 10/2012 | Holloway et al. |
| 2013/0023850 | A1 | 1/2013 | Imran et al. |
| 2014/0015078 | A1 | 1/2014 | Huai et al. |
| 2014/0069424 | A1 | 3/2014 | Poston et al. |
| 2014/0150783 | A1 | 6/2014 | Liu |
| 2014/0158129 | A1 | 6/2014 | Pratt et al. |
| 2014/0261488 | A1 | 9/2014 | Tucker |
| 2014/0366896 | A1 | 12/2014 | Li et al. |
| 2014/0373857 | A1 | 12/2014 | Steinberg |
| 2015/0020831 | A1 | 1/2015 | Weigensberg et al. |
| 2015/0136158 | A1 | 5/2015 | Stevens et al. |
| 2015/0173417 | A1 | 6/2015 | Gennrich et al. |
| 2015/0173421 | A1 | 6/2015 | Hsieh |
| 2015/0223522 | A1 | 8/2015 | Ampolini et al. |
| 2015/0245669 | A1 | 9/2015 | Cadieux et al. |
| 2015/0296889 | A1 | 10/2015 | Liu |
| 2015/0305409 | A1 | 10/2015 | Verleur et al. |
| 2016/0020048 | A1 | 1/2016 | Ware |
| 2016/0021934 | A1 | 1/2016 | Cadieux et al. |
| 2016/0109115 | A1 | 4/2016 | Lipowicz |
| 2016/0150824 | A1 | 6/2016 | Memari et al. |
| 2016/0278436 | A1 | 9/2016 | Verleur et al. |
| 2016/0324217 | A1 | 11/2016 | Cameron |
| 2016/0325055 | A1 | 11/2016 | Cameron |
| 2016/0331022 | A1 | 11/2016 | Cameron |
| 2016/0331023 | A1 | 11/2016 | Cameron |
| 2016/0331024 | A1 | 11/2016 | Cameron |
| 2016/0331025 | A1 | 11/2016 | Cameron |
| 2016/0331026 | A1 | 11/2016 | Cameron |
| 2016/0331027 | A1 | 11/2016 | Cameron |
| 2016/0331034 | A1 | 11/2016 | Cameron |
| 2016/0331859 | A1 | 11/2016 | Cameron |
| 2016/0334119 | A1 | 11/2016 | Cameron |
| 2016/0334847 | A1 | 11/2016 | Cameron |
| 2016/0337141 | A1 | 11/2016 | Cameron |
| 2016/0337362 | A1 | 11/2016 | Cameron |
| 2016/0337444 | A1 | 11/2016 | Cameron |
| 2016/0356751 | A1 | 12/2016 | Blackley |
| 2016/0363570 | A1 | 12/2016 | Blackley |
| 2016/0363917 | A1 | 12/2016 | Blackley |
| 2016/0367925 | A1 | 12/2016 | Blackley |
| 2016/0370335 | A1 | 12/2016 | Blackley |
| 2016/0374395 | A1 | 12/2016 | Jordan et al. |
| 2017/0018000 | A1 | 1/2017 | Cameron |
| 2017/0020188 | A1 | 1/2017 | Cameron |
| 2017/0020195 | A1 | 1/2017 | Cameron |
| 2017/0020196 | A1 | 1/2017 | Cameron |
| 2017/0020197 | A1 | 1/2017 | Cameron |
| 2017/0027221 | A1 | 2/2017 | Liu |
| 2017/0027229 | A1 | 2/2017 | Cameron |
| 2017/0027233 | A1 | 2/2017 | Mironov |
| 2017/0028178 | A1 | 2/2017 | Skoda |
| 2017/0030882 | A1 | 2/2017 | Skoda |
| 2017/0042230 | A1 | 2/2017 | Cameron |
| 2017/0042231 | A1 | 2/2017 | Cameron |
| 2017/0045994 | A1 | 2/2017 | Murison et al. |
| 2017/0046357 | A1 | 2/2017 | Cameron |
| 2017/0046738 | A1 | 2/2017 | Cameron |
| 2017/0055575 | A1 | 3/2017 | Wilke et al. |
| 2017/0055588 | A1 | 3/2017 | Cameron |
| 2017/0079330 | A1 | 3/2017 | Mironov et al. |
| 2017/0086496 | A1 | 3/2017 | Cameron |
| 2017/0086497 | A1 | 3/2017 | Cameron |
| 2017/0086503 | A1 | 3/2017 | Cameron |
| 2017/0086504 | A1 | 3/2017 | Cameron |
| 2017/0086507 | A1 | 3/2017 | Rado |
| 2017/0091853 | A1 | 3/2017 | Cameron |
| 2017/0092106 | A1 | 3/2017 | Cameron |
| 2017/0093960 | A1 | 3/2017 | Cameron |
| 2017/0093981 | A1 | 3/2017 | Cameron |
| 2017/0105452 | A1 | 4/2017 | Mironov et al. |
| 2017/0119050 | A1 | 5/2017 | Blandino et al. |
| 2017/0119058 | A1 | 5/2017 | Cameron |
| 2017/0135407 | A1 | 5/2017 | Cameron |
| 2017/0135408 | A1 | 5/2017 | Cameron |
| 2017/0135409 | A1 | 5/2017 | Cameron |
| 2017/0135411 | A1 | 5/2017 | Cameron |
| 2017/0135412 | A1 | 5/2017 | Cameron |
| 2017/0136193 | A1 | 5/2017 | Cameron |
| 2017/0136194 | A1 | 5/2017 | Cameron |
| 2017/0136196 | A1 | 5/2017 | Davidson et al. |
| 2017/0136301 | A1 | 5/2017 | Cameron |
| 2017/0143041 | A1 | 5/2017 | Batista et al. |
| 2017/0095004 | A1 | 6/2017 | Liu |
| 2017/0150755 | A1 | 6/2017 | Batista |
| 2017/0172208 | A1 | 6/2017 | Mironov |
| 2017/0181467 | A1 | 6/2017 | Cameron |
| 2017/0181474 | A1 | 6/2017 | Cameron et al. |
| 2017/0181475 | A1 | 6/2017 | Cameron |
| 2017/0185364 | A1 | 6/2017 | Cameron |
| 2017/0188636 | A1 | 7/2017 | Li et al. |
| 2017/0231276 | A1 | 8/2017 | Mironov et al. |
| 2017/0231277 | A1 | 8/2017 | Mironov et al. |
| 2017/0231278 | A1 | 8/2017 | Mironov et al. |
| 2017/0231283 | A1 | 8/2017 | Gadas |
| 2017/0238617 | A1 | 8/2017 | Scatterday |
| 2017/0266397 | A1 | 9/2017 | Mayle et al. |
| 2017/0273358 | A1 | 9/2017 | Batista et al. |
| 2017/0302324 | A1 | 10/2017 | Stanimirovic et al. |
| 2017/0303590 | A1 | 10/2017 | Cameron et al. |
| 2017/0303593 | A1 | 10/2017 | Cameron et al. |
| 2017/0303594 | A1 | 10/2017 | Cameron et al. |
| 2017/0309091 | A1 | 10/2017 | Cameron et al. |
| 2017/0332702 | A1 | 11/2017 | Cameron et al. |
| 2018/0077967 | A1 | 3/2018 | Hatton et al. |
| 2018/0160735 | A1 | 6/2018 | Borkovec et al. |
| 2018/0168227 | A1 | 6/2018 | Fraser et al. |
| 2018/0177231 | A1 | 6/2018 | Woodbine et al. |
| 2018/0177240 | A1 | 6/2018 | Duque et al. |
| 2018/0184712 | A1 | 7/2018 | Fraser et al. |
| 2018/0184722 | A1 | 7/2018 | Murison et al. |
| 2018/0192700 | A1 | 7/2018 | Fraser et al. |
| 2018/0343925 | A1 | 12/2018 | Wensley et al. |
| 2019/0069601 | A1 | 3/2019 | Qiu |
| 2019/0230985 | A1 | 8/2019 | Chan et al. |
| 2020/0000146 | A1 | 1/2020 | Anderson et al. |
| 2020/0037669 | A1 | 2/2020 | Bowen et al. |
| 2020/0107585 | A1 | 4/2020 | Atkins et al. |

(56) References Cited

U.S. PATENT DOCUMENTS

| | | |
|---|---|---|
| 2020/0113245 A1 | 4/2020 | Rosser et al. |
| 2020/0120991 A1 | 4/2020 | Hatton et al. |
| 2020/0120993 A1 | 4/2020 | Atkins et al. |
| 2020/0127475 A1 | 4/2020 | Cheung et al. |
| 2020/0138118 A1 | 5/2020 | Stratton |
| 2022/0117296 A1* | 4/2022 | Lahoud .................. A24F 40/90 |
| 2023/0118045 A1* | 4/2023 | Danek .................. A61M 11/005 |
| | | 131/329 |
| 2023/0346014 A1* | 11/2023 | Lahoud .................. A24F 40/53 |
| 2024/0423289 A1* | 12/2024 | Minato .................. A24F 40/57 |

FOREIGN PATENT DOCUMENTS

| | | |
|---|---|---|
| JP | 2017500011 A | 1/2017 |
| JP | 2018504926 A | 2/2018 |
| KZ | 31968 B | 4/2017 |
| RU | 2606326 C2 | 1/2017 |
| RU | 2620951 C1 | 5/2017 |
| WO | WO-2006021153 A1 | 3/2006 |
| WO | WO-2012026963 A2 | 3/2012 |
| WO | WO-2012134117 A2 | 10/2012 |
| WO | WO-2013020220 A1 | 2/2013 |
| WO | WO-2014067236 A1 | 5/2014 |
| WO | WO-2014068504 A2 | 5/2014 |
| WO | WO-2015037925 A1 | 3/2015 |
| WO | WO-2015149330 A1 | 10/2015 |
| WO | WO-2015149332 A1 | 10/2015 |
| WO | WO-2015161557 A1 | 10/2015 |
| WO | WO-2015172390 A1 | 11/2015 |
| WO | WO-2015180027 A1 | 12/2015 |
| WO | WO-2016033783 A1 | 3/2016 |
| WO | WO-2016041140 A1 | 3/2016 |
| WO | WO-2016101144 A1 | 6/2016 |
| WO | WO-2016119225 A1 | 8/2016 |
| WO | WO-2016124017 A1 | 8/2016 |
| WO | WO-2016141555 A1 | 9/2016 |
| WO | WO-2016149932 A1 | 9/2016 |
| WO | WO-2016172847 A1 | 11/2016 |
| WO | WO-2016187695 A1 | 12/2016 |
| WO | WO-2016193705 A2 | 12/2016 |
| WO | WO-2017001352 A2 | 1/2017 |
| WO | WO-2017054424 A1 | 4/2017 |
| WO | WO-2017068098 A1 | 4/2017 |
| WO | WO-2017068100 A1 | 4/2017 |
| WO | WO-2017085242 A1 | 5/2017 |
| WO | WO-2017109448 A2 | 6/2017 |
| WO | WO-2017122196 A1 | 7/2017 |
| WO | WO-2017137510 A1 | 8/2017 |
| WO | WO-2017141017 A1 | 8/2017 |
| WO | WO-2017205838 A1 | 11/2017 |
| WO | WO-2020006305 A1 | 1/2020 |
| WO | WO-2020023547 A1 | 1/2020 |

OTHER PUBLICATIONS

Zeeshan, et al. (Jul. 1, 2017) "Hydromagnetic Blood Flow of Sisko Fluid in a Non-uniform Channel Induced by Peristaltic Wave", Communications in Theoretical Physics, 68(1):103-110.

* cited by examiner

CARTRIDGES FOR VAPORIZER DEVICES

CROSS-REFERENCE TO RELATED APPLICATIONS

This application is a continuation application of U.S. patent application Ser. No. 16/674,762 filed on Nov. 5, 2019, and entitled "Cartridge For Vaporizer Devices," which claims priority to U.S. Provisional Patent Application No. 62/755,965 filed on Nov. 5, 2018, and entitled "Cartridges For Vaporizer Devices," the disclosures of all of which are incorporated herein by reference in their entireties.

TECHNICAL FIELD

The subject matter described herein relates to vaporizer devices, including vaporizer cartridges.

BACKGROUND

Vaporizer devices, which can also be referred to as vaporizers, electronic vaporizer devices, or e-vaporizer devices, can be used for delivery of an aerosol (for example, a vapor-phase and/or condensed-phase material suspended in a stationary or moving mass of air or some other gas carrier) containing one or more active ingredients by inhalation of the aerosol by a user of the vaporizing device. For example, electronic nicotine delivery systems (ENDS) include a class of vaporizer devices that are battery powered and that can be used to simulate the experience of smoking, but without burning of tobacco or other substances. Vaporizer devices are gaining increasing popularity both for prescriptive medical use, in delivering medicaments, and for consumption of tobacco, nicotine, and other plant-based materials. Vaporizer devices can be portable, self-contained, and/or convenient for use.

In use of a vaporizer device, the user inhales an aerosol, colloquially referred to as "vapor," which can be generated by a heating element that vaporizes (e.g., causes a liquid or solid to at least partially transition to the gas phase) a vaporizable material, which can be liquid, a solution, a solid, a paste, a wax, and/or any other form compatible for use with a specific vaporizer device. The vaporizable material used with a vaporizer device can be provided within a cartridge for example, a separable part of the vaporizer device that contains vaporizable material) that includes an outlet (for example, a mouthpiece) for inhalation of the aerosol by a user.

To receive the inhalable aerosol generated by a vaporizer device, a user may, in certain examples, activate the vaporizer device by taking a puff, by pressing a button, and/or by some other approach. A puff as used herein can refer to inhalation by the user in a manner that causes a volume of air to be drawn into the vaporizer device such that the inhalable aerosol is generated by a combination of the vaporized vaporizable material with the volume of air.

An approach by which a vaporizer device generates an inhalable aerosol from a vaporizable material involves heating the vaporizable material in a vaporization chamber (e.g., a heater chamber) to cause the vaporizable material to be converted to the gas (or vapor) phase. A vaporization chamber can refer to an area or volume in the vaporizer device within which a heat source (for example, a conductive, convective, and/or radiative heat source) causes heating of a vaporizable material to produce a mixture of air and vaporized material to form a vapor for inhalation of the vaporizable material by a user of the vaporizer device.

Vaporizer devices can be controlled by one or more controllers, electronic circuits (for example, sensors, heating elements), and/or the like on the vaporizer device. Vaporizer devices can also wirelessly communicate with an external controller for example, a computing device such as a smartphone).

In some implementations, the vaporizable material can be drawn out of a reservoir and into the vaporization chamber via a wicking element (e.g., a wick). Drawing of the vaporizable material into the vaporization chamber can be at least partially due to capillary action provided by the wicking element as the wicking element pulls the vaporizable material along the wicking element in the direction of the vaporization chamber. However, as vaporizable material is drawn out of the reservoir, the pressure inside the reservoir is reduced, thereby creating a vacuum and acting against the capillary action. This can reduce the effectiveness of the wicking element to draw the vaporizable material into the vaporization chamber, thereby reducing the effectiveness of the vaporizer device to vaporize a desired amount of vaporizable material, such as when a user takes a puff on the vaporizer device. Furthermore, the vacuum created in the reservoir can ultimately result in the inability to draw all of the vaporizable material into the vaporization chamber, thereby wasting vaporizable material. As such, improved vaporizer devices and/or vaporization cartridges that improve upon or overcome these issues are desired.

SUMMARY

Aspects of the current subject matter relate to vaporizer devices and to cartridges for use in a vaporizer device.

In some variations, one or more of the following features may optionally be included in any feasible combination.

In one exemplary embodiment, a cartridge is provided and includes a first storage chamber and a second storage chamber, a vaporization chamber that includes an elongate member that is in fluid communication with the first storage chamber and the second storage chamber, a magnetic element, and a conductive element in selective communication with the magnetic element. The first storage chamber is configured to hold a first fraction of a vaporizable material and the second storage chamber is configured to hold a second fraction of the vaporizable material. The elongate member extends from a first end to a second end with a channel extending therebetween, and the elongate member is configured to receive the vaporizable material. The magnetic element is disposed within the channel of the elongate member. The magnetic element is configured to selectively oscillate between a first position and a second position so as to substantially control the flow of the vaporizable material into the elongate member. The conductive element is configured to generate a first motive force in response to receiving a first electric current to drive the magnetic element from the first position to the second position and is configured to generate a second motive force in response to receiving a second electric current to drive the magnetic element from the second position to the first position, in which the second direction is opposite of the first direction. The conductive element is further configured to substantially vaporize the vaporizable material within the elongate member to a vaporized material in response to receiving the first electric current and in response to receiving the second electric current.

The conductive element can have a variety of configurations. For example, in some embodiments, the conductive element can be a coil that is substantially wound about at least a portion of the elongate member. In some embodiments, the conductive element can be configured to produce an alternating magnetic field.

In some embodiments, the first electric current can have a first polarity and the second electric current can have a second polarity that is opposite the first polarity.

In some embodiments, when in the first position, the magnetic element can be configured to prevent the first fraction of the vaporizable material from flowing into the elongate member, and when in the second position, the magnetic element can be configured to prevent the second fraction of the vaporizable material from flowing into the elongate member. In certain embodiments, a portion of the first fraction of the vaporizable material can flow into the elongate member when the magnetic element is in the second position. In such embodiments, an inlet valve can be positioned at the first end of the elongate member, in which the inlet valve can be configured to substantially prevent backflow of the portion of the first fraction of the vaporizable material from the elongate member and into the first storage chamber. In certain embodiments, a portion of the second fraction of the vaporizable material can flow into the elongate member when the magnetic element is in the first position. In such embodiments, an inlet valve can be positioned at the second end of the elongate member, in which the inlet valve can be configured to substantially prevent backflow of the portion of the second fraction of the vaporizable material from the elongate member and into the second storage chamber.

The magnetic element can have a variety of configurations. For example, in some embodiments, the magnetic element can be a permanent magnet.

The vaporization chamber can have a variety of configurations. For example, in some embodiments, the vaporization chamber can define an airflow passageway that extends therethrough. The airflow passageway can be configured to allow the vaporized material to combine with an influx of air such that the vaporized material passes out of the vaporization chamber.

In another exemplary embodiment, a vaporizer device is provided and includes a vaporizer body and a cartridge that is selectively coupled to and removable from the vaporizer body. The cartridge includes a first storage chamber and a second storage chamber, a vaporization chamber that includes an elongate member that is in fluid communication with the first storage chamber and the second storage chamber, a magnetic element, and a conductive element in selective communication with the magnetic element. The first storage chamber is configured to hold a first fraction of a vaporizable material and the second storage chamber is configured to hold a second fraction of the vaporizable material. The elongate member extends from a first end to a second end with a channel extending therebetween, and the elongate member is configured to receive the vaporizable material. The magnetic element is disposed within the channel of the elongate member. The magnetic element is configured to selectively oscillate between a first position and a second position so as to substantially control the flow of the vaporizable material into the elongate member. The conductive element is configured to generate a first motive force in response to receiving a first electric current to drive the magnetic element from the first position to the second position and is configured to generate a second motive force in response to receiving a second electric current to drive the magnetic element from the second position to the first position, in which the second direction is opposite of the first direction. The conductive element is further configured to substantially vaporize the vaporizable material within the elongate member to a vaporized material in response to receiving the first electric current and in response to receiving the second electric current.

The vaporizer body can have a variety of configurations. For example, in some embodiments, the vaporizer body can include a power source.

The conductive element can have a variety of configurations. For example, in some embodiments, the conductive element can be configured to produce an alternating magnetic field.

In some embodiments, the first electric current can have a first polarity and the second electric current can have a second polarity that is opposite the first polarity.

In some embodiments, when in the first position, the magnetic element can be configured to prevent the first fraction of the vaporizable material from flowing into the elongate member, and when in the second position, the magnetic element can be configured to prevent the second fraction of the vaporizable material from flowing into the elongate member. In certain embodiments, a portion of the first fraction of the vaporizable material can flow into the elongate member when the magnetic element is in the second position. In such embodiments, an inlet valve can be positioned at the first end of the elongate member, in which the inlet valve can be configured to substantially prevent backflow of the portion of the first fraction of the vaporizable material from the elongate member and into the first storage chamber. In certain embodiments, a portion of the second fraction of the vaporizable material can flow into the elongate member when the magnetic element is in the first position. In such embodiments, an inlet valve can be positioned at the second end of the elongate member, in which the inlet valve can be configured to substantially prevent backflow of the portion of the second fraction of the vaporizable material from the elongate member and into the second storage chamber.

The details of one or more variations of the subject matter described herein are set forth in the accompanying drawings and the description below. Other features and advantages of the subject matter described herein will be apparent from the description and drawings, and from the claims. The claims that follow this disclosure are intended to define the scope of the protected subject matter.

BRIEF DESCRIPTION OF THE DRAWINGS

The accompanying drawings, which are incorporated into and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Implementations of the current subject matter include methods, apparatuses, articles of manufacture, and systems relating to vaporization of one or more materials for inhalation by a user. Example implementations include vaporizer devices and systems including vaporizer devices. The term "vaporizer device" as used in the following description and claims refers to any of a self-contained apparatus, an apparatus that includes two or more separable parts (for example, a vaporizer body that includes a battery and other hardware, and a cartridge that includes a vaporizable material), and/or the like. A "vaporizer system," as used herein, can include one or more components, such as a vaporizer device. Examples of vaporizer devices consistent with implementations of the current subject matter include electronic vaporizers, electronic nicotine delivery systems (ENDS), and/or the like. In general, such vaporizer devices are hand-held devices that heat (such as by convection, conduction, radiation, and/or some combination thereof) a vaporizable material to provide an inhalable dose of the material.

The vaporizable material used with a vaporizer device can be provided within a cartridge (for example, a part of the vaporizer device that contains the vaporizable material in a reservoir or other container) which can be refillable when empty, or disposable such that a new cartridge containing additional vaporizable material of a same or different type can be used). A vaporizer device can be a cartridge-using vaporizer device, a cartridge-less vaporizer device, or a multi-use vaporizer device capable of use with or without a cartridge. For example, a vaporizer device can include a heating chamber (for example, an oven or other region in which material is heated by a heating element) configured to receive a vaporizable material directly into the heating chamber, and/or a reservoir or the like for containing the vaporizable material.

In some implementations, a vaporizer device can be configured for use with a liquid vaporizable material (for example, a carrier solution in which an active and/or inactive ingredient(s) are suspended or held in solution, or a liquid form of the vaporizable material itself). The liquid vaporizable material can be capable of being completely vaporized. Alternatively, at least a portion of the liquid vaporizable material can remain after all of the material suitable for inhalation has been vaporized.

Figure 1A:
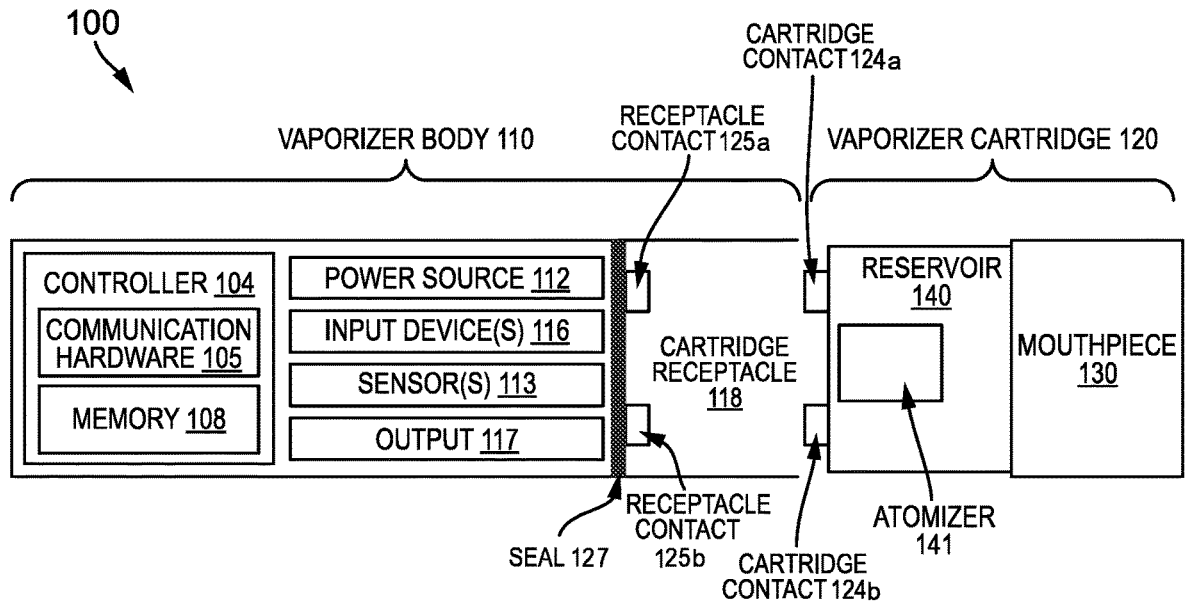
FIG. 1A is a block diagram of a vaporizer device.

Referring to the block diagram of FIG. 1A, a vaporizer device 100 can include a power source 112 (for example, a battery, which can be a rechargeable battery), and a controller 104 (for example, a processor, circuitry, etc. capable of executing logic) for controlling delivery of heat to an atomizer 141 to cause a vaporizable material 102 to be converted from a condensed form (such as a liquid, a solution, a suspension, a part of an at least partially unprocessed plant material, etc.) to the gas phase. The controller 104 can be part of one or more printed circuit boards (PCBs) consistent with certain implementations of the current subject matter.

After conversion of the vaporizable material 102 to the gas phase, at least some of the vaporizable material 102 in the gas phase can condense to form particulate matter in at least a partial local equilibrium with the gas phase as part of an aerosol, which can form some or all of an inhalable dose provided by the vaporizer device 100 during a user's puff or draw on the vaporizer device 100. It should be appreciated that the interplay between gas and condensed phases in an aerosol generated by a vaporizer device 100 can be complex and dynamic, due to factors such as ambient temperature, relative humidity, chemistry, flow conditions in airflow paths (both inside the vaporizer device and in the airways of a human or other animal), and/or mixing of the vaporizable material 102 in the gas phase or in the aerosol phase with other air streams, which can affect one or more physical parameters of an aerosol. In some vaporizer devices, and particularly for vaporizer devices configured for delivery of volatile vaporizable materials, the inhalable dose can exist predominantly in the gas phase (for example, formation of condensed phase particles can be very limited).

The atomizer 141 in the vaporizer device 100 can be configured to vaporize a vaporizable material 102. The vaporizable material 102 can be a liquid. Examples of the vaporizable material 102 include neat liquids, suspensions, solutions, mixtures, and/or the like. The atomizer 141 can include a wicking element (i.e., a wick) configured to convey an amount of the vaporizable material 102 to a part of the atomizer 141 that includes a heating element (not shown in FIG. 1A).

For example, the wicking element can be configured to draw the vaporizable material 102 from a reservoir 140 configured to contain the vaporizable material 102, such that the vaporizable material 102 can be vaporized by heat delivered from a heating element. The wicking element can also optionally allow air to enter the reservoir 140 and replace the volume of vaporizable material 102 removed. In some implementations of the current subject matter, capillary action can pull vaporizable material 102 into the wick for vaporization by the heating element, and air can return to the reservoir 140 through the wick to at least partially equalize pressure in the reservoir 140. Other methods of allowing air back into the reservoir 140 to equalize pressure are also within the scope of the current subject matter.

As used herein, the terms "wick" or "wicking element" include any material capable of causing fluid motion via capillary pressure.

The heating element can include one or more of a conductive heater, a radiative heater, and/or a convective heater. One type of heating element is a resistive heating element, which can include a material (such as a metal or alloy, for example a nickel-chromium alloy, or a non-metallic resistor) configured to dissipate electrical power in the form of heat when electrical current is passed through one or more resistive segments of the heating element. In some implementations of the current subject matter, the atomizer 141 can include a heating element which includes a resistive coil or other heating element wrapped around, positioned within, integrated into a bulk shape of, pressed into thermal contact with, or otherwise arranged to deliver heat to a wicking element, to cause the vaporizable material 102 drawn from the reservoir 140 by the wicking element to be vaporized for subsequent inhalation by a user in a gas and/or a condensed (for example, aerosol particles or droplets) phase. Other wicking elements, heating elements, and/or atomizer assembly configurations are also possible.

The heating element can be activated in association with a user puffing (i.e., drawing, inhaling, etc.) on a mouthpiece 130 of the vaporizer device 100 to cause air to flow from an air inlet, along an airflow path that passes the atomizer 141 (i.e., wicking element and heating element). Optionally, air can flow from an air inlet through one or more condensation areas or chambers, to an air outlet in the mouthpiece 130. Incoming air moving along the airflow path moves over or through the atomizer 141, where vaporizable material 102 in the gas phase is entrained into the air. The heating element can be activated via the controller 104, which can optionally be a part of a vaporizer body 110 as discussed herein, causing current to pass from the power source 112 through a circuit including the resistive heating element, which is optionally part of a vaporizer cartridge 120 as discussed herein. As noted herein, the entrained vaporizable material 102 in the gas phase can condense as it passes through the remainder of the airflow path such that an inhalable dose of the vaporizable material 102 in an aerosol form can be delivered from the air outlet (for example, the mouthpiece 130) for inhalation by a user.

Activation of the heating element can be caused by automatic detection of a puff based on one or more signals generated by one or more of a sensor 113. The sensor 113 and the signals generated by the sensor 113 can include one or more of: a pressure sensor or sensors disposed to detect pressure along the airflow path relative to ambient pressure (or optionally to measure changes in absolute pressure), a motion sensor or sensors (for example, an accelerometer) of the vaporizer device 100, a flow sensor or sensors of the vaporizer device 100, a capacitive lip sensor of the vaporizer device 100, detection of interaction of a user with the vaporizer device 100 via one or more input devices 116 (for example, buttons or other tactile control devices of the vaporizer device 100), receipt of signals from a computing device in communication with the vaporizer device 100, and/or via other approaches for determining that a puff is occurring or imminent.

As discussed herein, the vaporizer device 100 consistent with implementations of the current subject matter can be configured to connect (such as, for example, wirelessly or via a wired connection) to a computing device (or optionally two or more devices) in communication with the vaporizer device 100. To this end, the controller 104 can include communication hardware 105. The controller 104 can also include a memory 108. The communication hardware 105 can include firmware and/or can be controlled by software for executing one or more cryptographic protocols for the communication.

A computing device can be a component of a vaporizer system that also includes the vaporizer device 100, and can include its own hardware for communication, which can establish a wireless communication channel with the communication hardware 105 of the vaporizer device 100. For example, a computing device used as part of a vaporizer system can include a general-purpose computing device (such as a smartphone, a tablet, a personal computer, some other portable device such as a smartwatch, or the like) that executes software to produce a user interface for enabling a user to interact with the vaporizer device 100. In other implementations of the current subject matter, such a device used as part of a vaporizer system can be a dedicated piece of hardware such as a remote control or other wireless or wired device having one or more physical or soft (i.e., configurable on a screen or other display device and selectable via user interaction with a touch-sensitive screen or some other input device like a mouse, pointer, trackball, cursor buttons, or the like) interface controls. The vaporizer device 100 can also include one or more outputs 117 or devices for providing information to the user. For example, the outputs 117 can include one or more light emitting diodes (LEDs) configured to provide feedback to a user based on a status and/or mode of operation of the vaporizer device 100.

In the example in which a computing device provides signals related to activation of the resistive heating element, or in other examples of coupling of a computing device with the vaporizer device 100 for implementation of various control or other functions, the computing device executes one or more computer instruction sets to provide a user interface and underlying data handling. In one example, detection by the computing device of user interaction with one or more user interface elements can cause the computing device to signal the vaporizer device 100 to activate the heating element to reach an operating temperature for creation of an inhalable dose of vapor/aerosol. Other functions of the vaporizer device 100 can be controlled by interaction of a user with a user interface on a computing device in communication with the vaporizer device 100.

The temperature of a resistive heating element of the vaporizer device 100 can depend on a number of factors, including an amount of electrical power delivered to the resistive heating element and/or a duty cycle at which the electrical power is delivered, conductive heat transfer to other parts of the electronic vaporizer device 100 and/or to the environment, latent heat losses due to vaporization of the vaporizable material 102 from the wicking element and/or the atomizer 141 as a whole, and convective heat losses due to airflow (i.e., air moving across the heating element or the atomizer 141 as a whole when a user inhales on the vaporizer device 100). As noted herein, to reliably activate the heating element or heat the heating element to a desired temperature, the vaporizer device 100 may, in some implementations of the current subject matter, make use of signals from the sensor 113 (for example, a pressure sensor) to determine when a user is inhaling. The sensor 113 can be positioned in the airflow path and/or can be connected (for example, by a passageway or other path) to an airflow path containing an inlet for air to enter the vaporizer device 100 and an outlet via which the user inhales the resulting vapor and/or aerosol such that the sensor 113 experiences changes (for example, pressure changes) concurrently with air passing through the vaporizer device 100 from the air inlet to the air outlet. In some implementations of the current subject matter, the heating element can be activated in association with a user's puff, for example by automatic detection of the puff, or by the sensor 113 detecting a change (such as a pressure change) in the airflow path.

The sensor 113 can be positioned on or coupled to (i.e., electrically or electronically connected, either physically or via a wireless connection) the controller 104 (for example, a printed circuit board assembly or other type of circuit board). To take measurements accurately and maintain durability of the vaporizer device 100, it can be beneficial to provide a seal 127 resilient enough to separate an airflow path from other parts of the vaporizer device 100. The seal 127, which can be a gasket, can be configured to at least partially surround the sensor 113 such that connections of the sensor 113 to the internal circuitry of the vaporizer device 100 are separated from a part of the sensor 113 exposed to the airflow path. In an example of a cartridge-based vaporizer device, the seal 127 can also separate parts of one or more electrical connections between the vaporizer body 110 and the vaporizer cartridge 120. Such arrangements of the seal 127 in the vaporizer device 100 can be helpful in mitigating against potentially disruptive impacts on vaporizer components resulting from interactions with environmental factors such as water in the vapor or liquid phases, other fluids such as the vaporizable material 102, etc., and/or to reduce the escape of air from the designated airflow path in the vaporizer device 100. Unwanted air, liquid or other fluid passing and/or contacting circuitry of the vaporizer device 100 can cause various unwanted effects, such as altered pressure readings, and/or can result in the buildup of unwanted material, such as moisture, excess vaporizable material 102, etc., in parts of the vaporizer device 100 where they can result in poor pressure signal, degradation of the sensor 113 or other components, and/or a shorter life of the vaporizer device 100. Leaks in the seal 127 can also result in a user inhaling air that has passed over parts of the vaporizer device 100 containing, or constructed of, materials that may not be desirable to be inhaled.

In some implementations, the vaporizer body 110 includes the controller 104, the power source 112 (for example, a battery), one more of the sensor 113, charging contacts (such as those for charging the power source 112), the seal 127, and a cartridge receptacle 118 configured to receive the vaporizer cartridge 120 for coupling with the vaporizer body 110 through one or more of a variety of attachment structures. In some examples, the vaporizer cartridge 120 includes the reservoir 140 for containing the vaporizable material 102, and the mouthpiece 130 has an aerosol outlet for delivering an inhalable dose to a user. The vaporizer cartridge 120 can include the atomizer 141 having a wicking element and a heating element. Alternatively, one or both of the wicking element and the heating element can be part of the vaporizer body 110. In implementations in which any part of the atomizer 141 (i.e., heating element and/or wicking element) is part of the vaporizer body 110, the vaporizer device 100 can be configured to supply vaporizable material 102 from the reservoir 140 in the vaporizer cartridge 120 to the part(s) of the atomizer 141 included in the vaporizer body 110.

In an embodiment of the vaporizer device 100 in which the power source 112 is part of the vaporizer body 110, and a heating element is disposed in the vaporizer cartridge 120 and configured to couple with the vaporizer body 110, the vaporizer device 100 can include electrical connection features (for example, means for completing a circuit) for completing a circuit that includes the controller 104 (for example, a printed circuit board, a microcontroller, or the like), the power source 112, and the heating element (for example, a heating element within the atomizer 141). These features can include one or more contacts (referred to herein as cartridge contacts 124a and 124b) on a bottom surface of the vaporizer cartridge 120 and at least two contacts (referred to herein as receptacle contacts 125a and 125b) disposed near a base of the cartridge receptacle 118 of the vaporizer device 100 such that the cartridge contacts 124a and 124b and the receptacle contacts 125a and 125b make electrical connections when the vaporizer cartridge 120 is inserted into and coupled with the cartridge receptacle 118. The circuit completed by these electrical connections can allow delivery of electrical current to a heating element and can further be used for additional functions, such as measuring a resistance of the heating element for use in determining and/or controlling a temperature of the heating element based on a thermal coefficient of resistivity of the heating element.

In some implementations of the current subject matter, the cartridge contacts 124a and 124b and the receptacle contacts 125a and 125b can be configured to electrically connect in either of at least two orientations. In other words, one or more circuits necessary for operation of the vaporizer device 100 can be completed by insertion of the vaporizer cartridge 120 into the cartridge receptacle 118 in a first rotational orientation (around an axis along which the vaporizer cartridge 120 is inserted into the cartridge receptacle 118 of the vaporizer body 110) such that the cartridge contact 124a is electrically connected to the receptacle contact 125a and the cartridge contact 124b is electrically connected to the receptacle contact 125b. Furthermore, the one or more circuits necessary for operation of the vaporizer device 100 can be completed by insertion of the vaporizer cartridge 120 in the cartridge receptacle 118 in a second rotational orientation such cartridge contact 124a is electrically connected to the receptacle contact 125b and cartridge contact 124b is electrically connected to the receptacle contact 125a.

For example, the vaporizer cartridge 120 or at least the insertable end 122 of the vaporizer cartridge 120 can be symmetrical upon a rotation of 180° around an axis along which the vaporizer cartridge 120 is inserted into the cartridge receptacle 118. In such a configuration, the circuitry of the vaporizer device 100 can support identical operation regardless of which symmetrical orientation of the vaporizer cartridge 120 occurs.

In one example of an attachment structure for coupling the vaporizer cartridge 120 to the vaporizer body 110, the vaporizer body 110 includes one or more detents (for example, dimples, protrusions, etc.) protruding inwardly from an inner surface of the cartridge receptacle 118, additional material (such as metal, plastic, etc.) formed to include a portion protruding into the cartridge receptacle 118, and/or the like. One or more exterior surfaces of the vaporizer cartridge 120 can include corresponding recesses (not shown in FIG. 1A) that can fit and/or otherwise snap over such detents or protruding portions when the vaporizer cartridge 120 is inserted into the cartridge receptacle 118 on the vaporizer body 110. When the vaporizer cartridge 120 and the vaporizer body 110 are coupled (e.g., by insertion of the vaporizer cartridge 120 into the cartridge receptacle 118 of the vaporizer body 110), the detents or protrusions of the vaporizer body 110 can fit within and/or otherwise be held within the recesses of the vaporizer cartridge 120, to hold the vaporizer cartridge 120 in place when assembled. Such an assembly can provide enough support to hold the vaporizer cartridge 120 in place to ensure good contact between the cartridge contacts 124a and 124b and the receptacle contacts 125a and 125b, while allowing release of the vaporizer cartridge 120 from the vaporizer body 110 when a user pulls with reasonable force on the vaporizer cartridge 120 to disengage the vaporizer cartridge 120 from the cartridge receptacle 118.

In some implementations, the vaporizer cartridge 120, or at least an insertable end 122 of the vaporizer cartridge 120 configured for insertion in the cartridge receptacle 118, can have a non-circular cross section transverse to the axis along which the vaporizer cartridge 120 is inserted into the cartridge receptacle 118. For example, the non-circular cross section can be approximately rectangular, approximately elliptical (i.e., have an approximately oval shape), non-rectangular but with two sets of parallel or approximately parallel opposing sides (i.e., having a parallelogram-like shape), or other shapes having rotational symmetry of at least order two. In this context, approximate shape indicates that a basic likeness to the described shape is apparent, but that sides of the shape in question need not be completely linear and vertices need not be completely sharp. Rounding of both or either of the edges or the vertices of the crosssectional shape is contemplated in the description of any non-circular cross section referred to herein.

The cartridge contacts 124a and 124b and the receptacle contacts 125a and 125b can take various forms. For example, one or both sets of contacts can include conductive pins, tabs, posts, receiving holes for pins or posts, or the like. Some types of contacts can include springs or other features to facilitate better physical and electrical contact between the contacts on the vaporizer cartridge 120 and the vaporizer body 110. The electrical contacts can optionally be gold-plated, and/or include other materials.

Figure 1B:
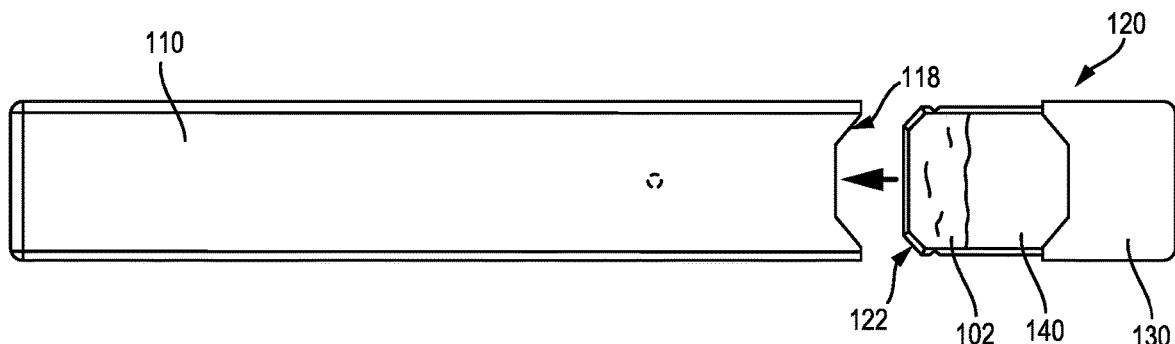
FIG. 1B is a top view of an embodiment of a vaporizer device, showing a vaporizer cartridge separated from a vaporizer device body.
Figure 1C:
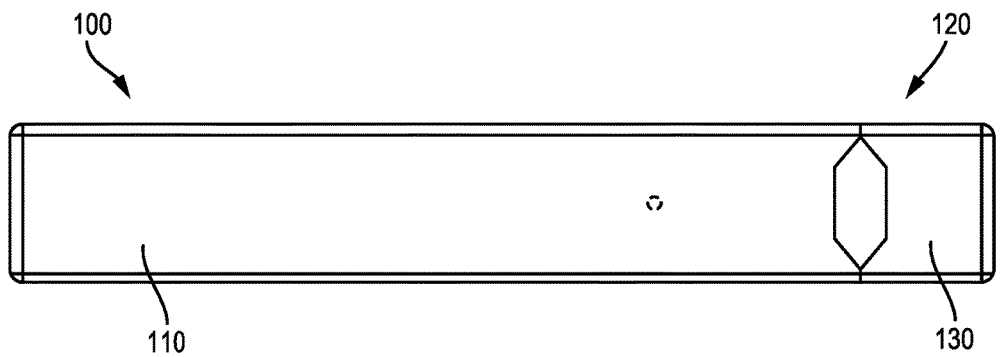
FIG. 1C is a top view of the vaporizer device of FIG. 1B, showing the vaporizer cartridge coupled to the vaporizer device body.
Figure 1D:
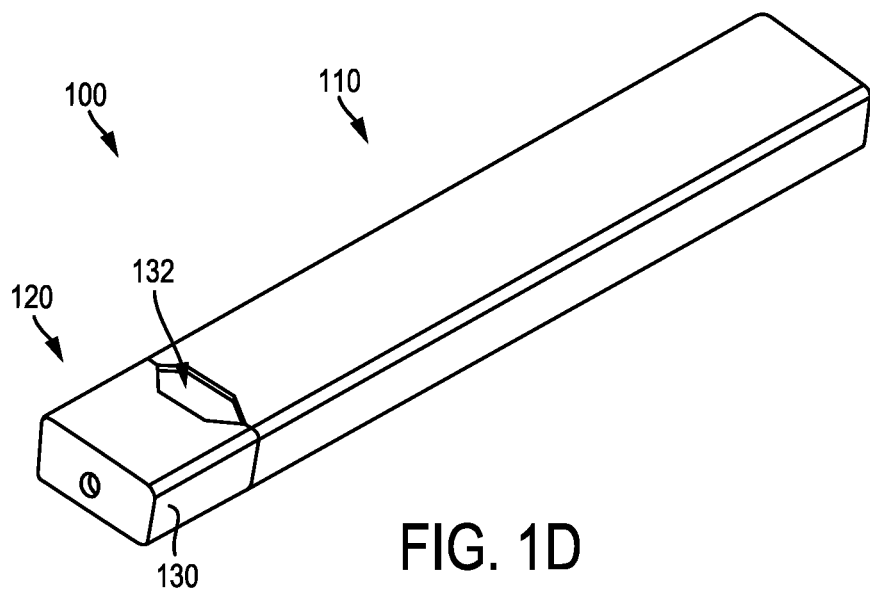
FIG. 1D is a perspective view of the vaporizer device of FIG. 1C.

FIGS. 1B-1D illustrate an embodiment of the vaporizer body 110 having a cartridge receptacle 118 into which the vaporizer cartridge 120 can be releasably inserted. FIGS. 1B and 1C show top views of the vaporizer device 100 illustrating the vaporizer cartridge 120 being positioned for insertion and inserted, respectively, into the vaporizer body 110. FIG. 1D illustrates the reservoir 140 of the vaporizer cartridge 120 being formed in whole or in part from translucent material such that a level of the vaporizable material 102 is visible from a window 132 (e.g., translucent material) along the vaporizer cartridge 120. The vaporizer cartridge 120 can be configured such that the window 132 remains visible when insertably received by the vaporizer cartridge receptacle 118 of the vaporizer body 110. For example, in one exemplary configuration, the window 132 can be disposed between a bottom edge of the mouthpiece 130 and a top edge of the vaporizer body 110 when the vaporizer cartridge 120 is coupled with the cartridge receptacle 118.

Figure 1E:
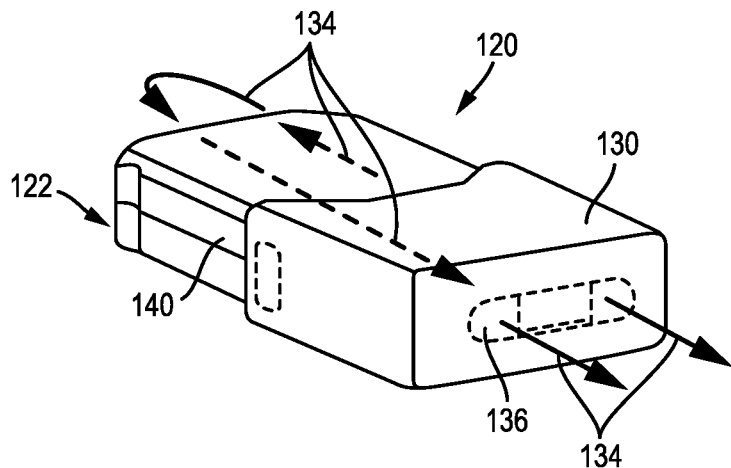
FIG. 1E is a perspective view of the vaporizer cartridge of FIG. 1B.

FIG. 1E illustrates an example airflow path 134 created during a puff by a user on the vaporizer device 100. The airflow path 134 can direct air to a vaporization chamber 150 (see FIG. 1F) contained in a wick housing where the air is combined with inhalable aerosol for delivery to a user via a mouthpiece 130, which can also be part of the vaporizer cartridge 120. For example, when a user puffs on the vaporizer device 100 device 100, air can pass between an outer surface of the vaporizer cartridge 120 (for example, window 132 shown in FIG. 1D) and an inner surface of the cartridge receptacle 118 on the vaporizer body 110. Air can then be drawn into the insertable end 122 of the vaporizer cartridge 120, through the vaporization chamber 150 that includes or contains the heating element and wick, and out through an outlet 136 of the mouthpiece 130 for delivery of the inhalable aerosol to a user.

As shown in FIG. 1E, this configuration causes air to flow down around the insertable end 122 of the vaporizer cartridge 120 into the cartridge receptacle 118 and then flow back in the opposite direction after passing around the insertable end 122 (e.g., an end opposite of the end including the mouthpiece 130) of the vaporizer cartridge 120 as it enters into the cartridge body toward the vaporization chamber 150. The airflow path 134 then travels through the interior of the vaporizer cartridge 120, for example via one or more tubes or internal channels (such as cannula 128 shown in FIG. 1F) and through one or more outlets (such as outlet 136) formed in the mouthpiece 130. The mouthpiece 130 can be a separable component of the vaporizer cartridge 120 or can be integrally formed with other component(s) of the vaporizer cartridge 120 (for example, formed as a unitary structure with the reservoir 140 and/or the like).

Figure 1F:
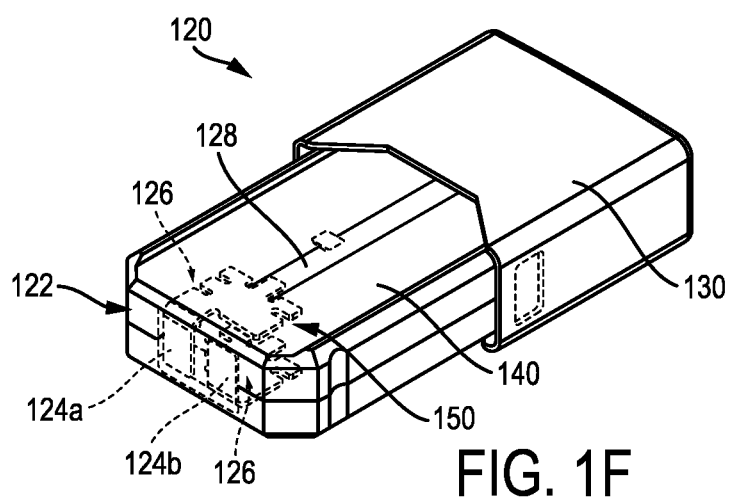
FIG. 1F is another perspective view of the vaporizer cartridge of FIG. 1E.

FIG. 1F shows additional features that can be included in the vaporizer cartridge 120 consistent with implementations of the current subject matter. For example, the vaporizer cartridge 120 can include a plurality of cartridge contacts (such as cartridge contacts 124a, 124b) disposed on the insertable end 122. The cartridge contacts 124a, 124b can optionally each be part of a single piece of metal that forms a conductive structure (such as conductive structure 126) connected to one of two ends of a resistive heating element. The conductive structure can optionally form opposing sides of a heating chamber and can act as heat shields and/or heat sinks to reduce transmission of heat to outer walls of the vaporizer cartridge 120. FIG. 1F also shows the cannula 128 within the vaporizer cartridge 120 that defines part of the airflow path 134 between the heating chamber formed between the conductive structure 126 and the mouthpiece 130.

As mentioned above, existing cartridges can include a wicking element that is generally configured to withdraw a vaporizable material from a reservoir housing such that the vaporizable material may be subsequently vaporized (e.g., by exposing the withdrawn vaporizable material to heat provided by a heating element). This withdrawing of the vaporizable material from the reservoir housing can be due, at least in part, to capillary action provided by the wick, which pulls the vaporizable material along the wick in the direction towards a vaporization chamber. As a result, the vaporizable material is fed into the wicking element by capillary action. However, the magnitude of capillary action can be at least partially contingent upon the wicking material itself (e.g., the type of wicking material, the dimensions of the wicking material (e.g., length), the absorption rate of the wicking material) and on the amount of vaporizable material contained within reservoir housing to replenish the wicking element. As a result, a consistent feed rate of vaporizable material into the vaporization chamber may be difficult to achieve and/or maintain due to changes in the magnitude of the capillary action present in the wick.

Under such circumstances, the effectiveness of the vaporization device to vaporize a desired amount of vaporizable material, such as when a user takes a puff on the vaporizer device, can be reduced. Various features and devices are described below that improve upon or overcome these issues. For example, various features are described herein that replace the wicking element with a pumping mechanism that is configured to pump the vaporizable material from the reservoir housing and into a vaporization chamber at a controlled feed rate. Implementing a pumping mechanism, as opposed to using a wicking element, may provide advantages and improvements relative to existing approaches, while also introducing additional benefits, as described herein.

The vaporizer cartridges described herein allow for controlled delivery of vaporizable material from a reservoir housing at a consistent feed rate. The vaporizer cartridges generally include a first storage chamber and a second storage chamber, each having vaporizable material disposed therein. The vaporizer cartridge further includes a vaporization chamber having an elongate member in fluid communication with the first storage chamber and the second storage chamber. As discussed in more detail below, a magnetic element is disposed within the elongate member and configured to selectively oscillate between a first position and a second position so as to substantially control the flow rate of the vaporizable material into the elongate member for vaporization. The magnetic element moves from the first position to the second position in response to a first motive force and from the second position back to the first position in response to a second motive force. These motive forces are generated by a conductive element that is in communication with the magnetic element. The conductive element is also configured to vaporize the vaporizable material within the elongate member. As such, the conductive element can be configured to produce the motive forces to oscillate the magnetic element as well as the heat needed to vaporize the vaporizable material.

Figure 2A:
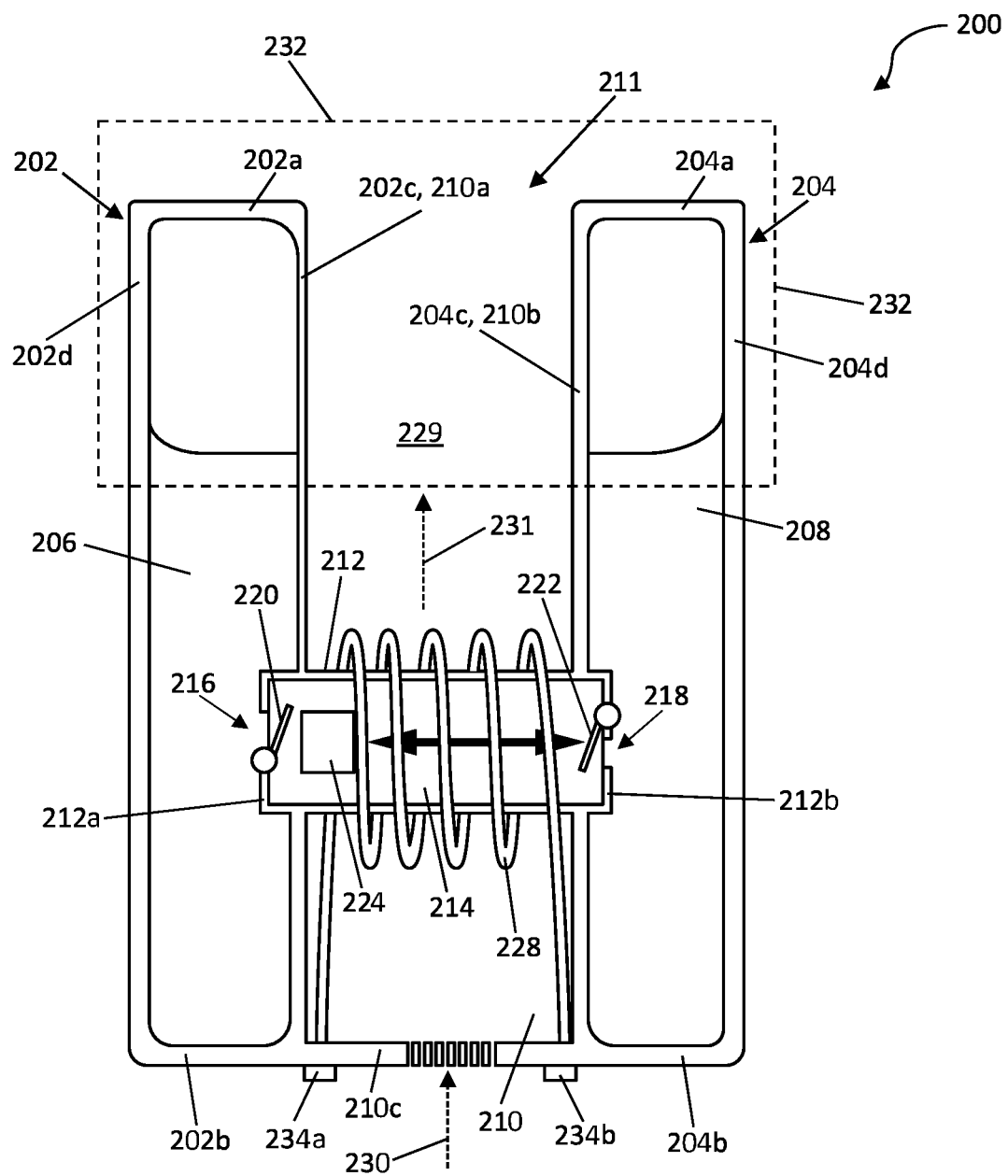
FIG. 2A illustrates a schematic of another embodiment of a vaporizer cartridge, the vaporizer cartridge having a magnetic element, showing the magnetic element in a first position.
Figure 2B:
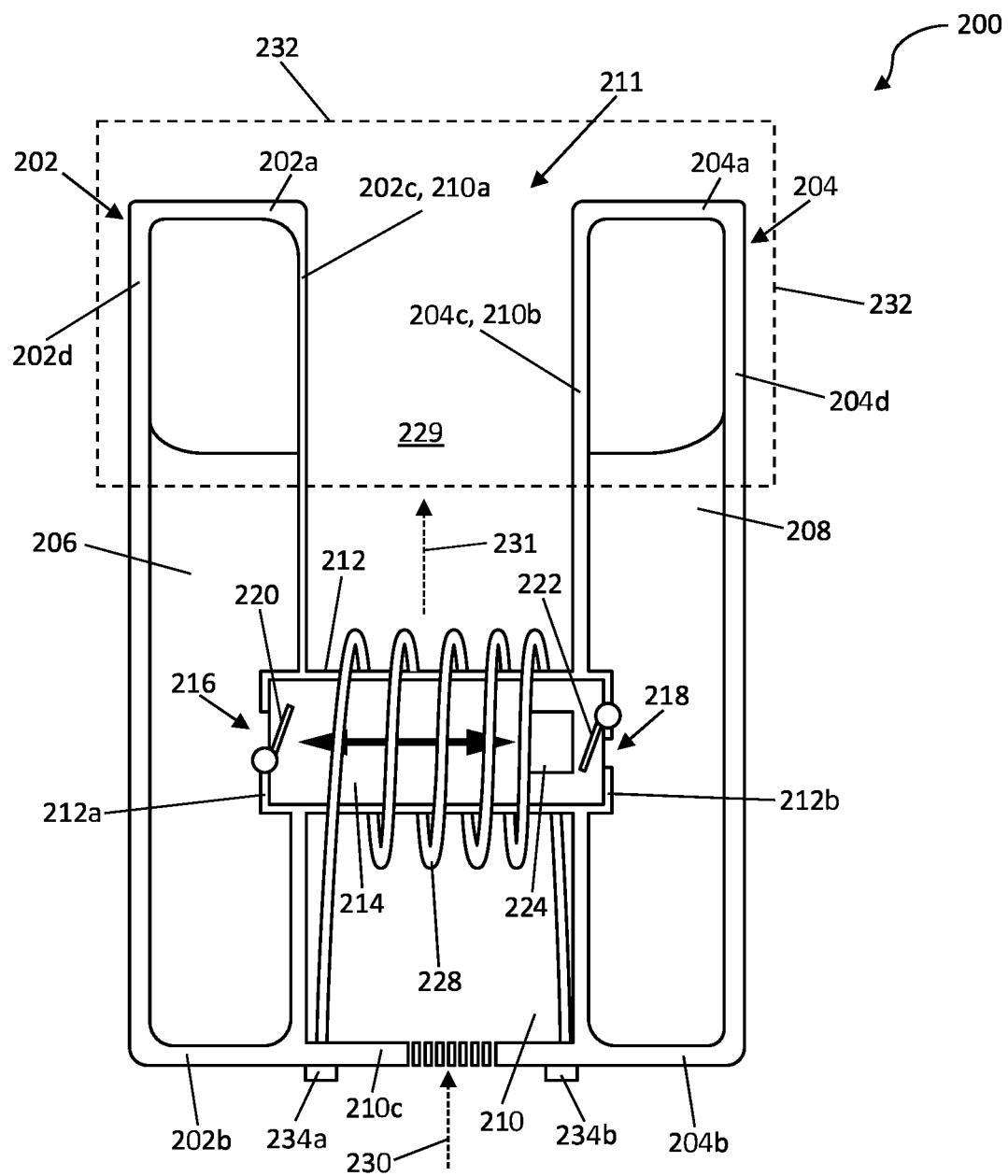
FIG. 2B illustrates the vaporizer cartridge of FIG. 2A, showing the magnetic element in a second position.

FIGS. 2A-2B illustrate an exemplary vaporizer cartridge 200 that can be selectively coupled to and removable from a vaporizer body, such as vaporizer body 110 shown in FIGS. 1A-1D). More specifically, the vaporizer cartridge 200 includes a vaporization chamber 210 having an elongate member 212 that is configured to receive a vaporizable material from a first storage chamber 202 and a second storage chamber 204, and a magnetic element 224 that is configured selectively oscillate between a first position and a second position within the elongate member 212 so as to substantially control the flow of the vaporizable material into the elongate member 212. For purposes of clarity, certain components of the vaporizer cartridge 200 are not illustrated.

As shown, the first storage chamber 202 and the second storage chamber 204 are spaced a distance apart from each other such that the first storage chamber 202 and the second storage chamber 204 are each defined by separate walls. That is, the first storage chamber 202 is defined by a first top wall 202a, a first bottom wall 202b that opposes the first top wall 202a, and two opposing first sidewalls 202c, 202d extending therebetween, and the second storage chamber 204 is defined by a second top wall 204a, a second bottom wall 204b that opposes the second top wall 204a, and two opposing second sidewalls 204c, 204d extending therebetween. The first storage chamber 202 is configured to hold a first fraction of a vaporizable material 206 and the second storage chamber 204 is configured to hold a second fraction of the vaporizable material 208. The first fraction of vaporizable material 206 and the second fraction of the vaporizable material 208 are collectively referred to herein as "vaporizable material."

While the shape and size of the first and second storage chamber 202, 204 can vary, each chamber, as shown in FIGS. 2A-2B, is substantially rectangular. The shape and size of the first storage chamber 202 and the second storage chamber 204 can also vary with respect to each other. Therefore, the shape and size of the first storage chamber 202 and the second storage chambers 204 are not limited by what is illustrated in FIGS. 2A-2B. Further, the first storage chamber 202 and/or the second storage chamber 204 can include at least one vent that is configured to substantially allow the passage of air into the respective storage chamber from the environment to thereby substantially maintain an inner pressure (e.g., an inner pressure that is substantially equal to ambient pressure) of the respective storage chamber. As such, the at least one vent can decrease or eliminate any negative pressure that is created as the vaporizable material flows out of the first storage chamber 202 or second storage chamber 204. This at least one vent can be a passive valve or an active valve.

In general, as discussed above, the vaporization chamber 210 includes the elongate member 212 that is configured to receive the vaporizable material from the first storage chamber 202 and the second storage chamber 204. As shown in FIGS. 2A-2B, the elongate member 212 extends from the first storage chamber 202 to the second storage chamber 204.

While the elongate member 212 can have a variety of configurations, the elongate member 212, as shown, is substantially cylindrical (e.g., in the form of a tube) and extends from a first end 212a to a second end 212b with a channel 214 extending therebetween. The first end 212a is positioned within the first storage chamber 202 and the second end 212b is positioned within the second storage chamber 204 such that the channel 214, and thus the elongate member 212, is in fluid communication with the first and second storage chambers 202, 204. The elongate member 212 can be formed of any suitable material that is configured to allow vaporized material (aerosol) to pass therethrough. As discussed in more detail below, the vaporizable material that flows into the elongate member 212 is vaporized to form a vaporized material (e.g., an aerosol) by the heat produced by the conductive element 228 in response to either the first electric current and the second electric current.

Each end of the elongate member 212 includes an inlet that is configured to allow the vaporizable material 206 to flow into the channel 214, and thus, the elongate member 212. As shown in FIGS. 2A-2B, the first end 212a includes a first inlet 216 and the second end 212b includes a second inlet 218 that allow the vaporizable material to flow into the channel 214 and, thus, into the elongate member 212 from the first storage chamber 202 and the second storage chamber 204, respectively, for vaporization into a vaporized material.

The first and second inlets 216, 218 can have a variety of shapes and/or sizes. For purposes of simplicity, only the first inlet 216 will be discussed herein with respect to size. However, a person skilled in the art will appreciate that the following discussion is equally applicable to the second inlet 218.

For example, the first inlet 216 can have a diameter that is sized to substantially prevent the passage of the first fraction of the vaporizable material 206 therethrough, when an internal pressure of the first storage chamber 202 is substantially equal to ambient pressure outside of the first storage chamber 202. That is, the first inlet 216 can include a diameter that is sized such that a surface tension of the first fraction of the vaporizable material 206 is created to thereby substantially prevent such vaporizable material from passing through, and thus, out of the first storage chamber 202, when the pressure is equalized across the first inlet 216.

Further, in some embodiments, one or more inlet valves can be positioned at the first end 212a and/or the second end 212b of the elongate member 212. The one or more inlet valves can be configured to substantially prevent the vaporizable material within the channel 214 of the elongate member 212 from flowing back into one of the storage chambers through one of the inlets of the elongate member 212. For example, as shown in FIGS. 2A-2B, a first inlet valve 220 is positioned at the first end 212a of the elongate member 212 to substantially prevent a portion of the first fraction of the vaporizable material 206 in the elongate member 212 from flowing back into the first storage chamber 202. As further shown in FIGS. 2A-2B, a second inlet valve 222 is positioned at the second end 212b of the elongate member 212 to substantially prevent a portion of the second fraction of the vaporizable material 208 in the elongate member 212 from flowing back into the second storage chamber 204. As such, the first inlet valve 220 and the second inlet valve 222 can each substantially function as a one-way valve that are configured to substantially allow an influx of vaporizable material into the elongate member 212 while also being configured to substantially inhibit backflow of the vaporizable material out of the elongate member 212.

As discussed above, a magnetic element 224 is disposed within the channel 214 of the elongate member 212. The magnetic element 224 is configured to selectively oscillate between a first position (e.g., as shown in 2A), and a second position (e.g., as shown in FIG. 2B). This oscillation between the first position and the second position can cause the vaporizable material 206 to flow alternately from the first storage chamber 202 and from the second storage chamber 204. For example, when in the first position (FIG. 2A), the magnetic element 224 is configured to substantially prevent the first fraction of the vaporizable material 206 from flowing into the elongate member 212, and when in the second position (FIG. 2B), the magnetic element 224 is configured to substantially prevent the second fraction of the vaporizable material 208 from flowing into the elongate member 212. As such, the oscillation of the magnetic element 224 substantially controls the delivery of the vaporizable material into the elongate member 212. Further, the magnetic element 224 in combination with the size of the inlets of the elongate member 212 can also control the flow rate of the vaporizable material into the elongate member 212. As a result, a consistent delivery rate of the vaporizable material can be delivered to the vaporization chamber 210 for vaporization.

The magnetic element 224 can have a variety of configurations and sizes. For example, as shown in FIGS. 2A-2B, the magnetic element 224 is substantially rectangular. Further, the magnetic element 224 can be formed of any suitable material that can be magnetized, e.g., iron, nickel, cobalt, and the like. In one embodiment, the magnetic element 224 is a permanent magnet.

As discussed above, in use, the magnetic element 224 moves from the first position to the second position in response to the first motive force and from the second position back to the first position in response to the second motive force. The first motive force and the second motive force are generated by the conductive element 228 in response to the conductive element 228 receiving a first electric current and a second electric current, respectively.

The conductive element 228 can have a variety of configurations that substantially allow the conductive element 228 to be in selective communication with the magnetic element 224 so as to effect oscillation of the magnetic element 224 in response to the first and second motive forces. For example, the conductive element 228, as shown in FIGS. 2A-2B, is a conductive coil that is substantially wound about the elongate member 212. The conductive element 228 can be formed from any suitable electrically and thermally conductive material, such as iron, carbon steel, stainless steel, aluminum, copper, brass, bronze, electrically conductive ceramic and polymer composites, or other materials capable of being inductively heated.

The conductive element 228 is connected to a power source, such as the power source 112 within vaporizer body 110 shown in FIGS. 1A-1D. The power source, when prompted (e.g., when a user puffs on a mouthpiece, such as mouthpiece 232 shown in FIGS. 2A-2B), supplies alternating currents (e.g., the first electric current and the second electric current having a reverse or opposite polarity of the first electric current) to the conductive element 228. For example, in some embodiments, the vaporizer cartridge 200 includes two or more cartridge contacts such as, for example, a first cartridge contact 234a and a second cartridge contact 234b. The two or more cartridge contacts can be configured to couple, for example, with the receptacle contacts 125a and 125b in order to form one or more electrical connections with the power source 112. The circuit completed by these electrical connections can allow delivery of electrical currents to the conductive element 228.

In response to the application of alternating currents, the conductive element 228 produces alternating magnetic fields. As such, these alternating magnetic fields act on the magnetic element 224 causing the magnetic element 224 to oscillate from the first position to the second position or vice versa in response to the applied current. That is, in use, when the conductive element 228 receives the first current, which has a first polarity, the conductive element 228 generates a first magnetic field that provides the first motive force to drive the magnetic element 224 from the first position to the second position, and when the conductive element 228 receives the second current, which has a second polarity that is opposite the first polarity, the conductive element 228 generates a second magnetic field that provides the second motive force to drive the magnetic element 224 from the second position to the first position Thus, the alternating currents applied to the conductive element 228 allow the conductive element 228 to produce alternating magnetic fields that drive the magnetic element 224.

Further, the alternating magnetic fields generated by the conductive element 228 pass through the elongate member 212 causing eddy currents. These eddy currents heat the elongate member 212 to a temperature that is at least substantially equal to the vaporization temperature of the vaporizable material. As a result, the portion of the vaporizable material (e.g., a portion of the first fraction of the vaporizable material 206 or of the second fraction of the vaporizable material 208) that flows into the elongate member 212 is then vaporized to form a vaporized material (e.g., aerosol). This vaporized material can then combine with, and be carried out of the vaporization chamber 210, by the air 230 passing through an airflow passageway, such as the airflow passageway 229, of the vaporization chamber 210. As such, the conductive element 228 can be configured to substantially produce the motive forces to drive the magnetic element 224 to allow flow of the vaporizable material into the elongate member 212 and to substantially vaporize the vaporizable material within the elongate member 212.

The first and/or second electric current applied to, and received by, the conductive material 228 can be adjusted, for example, by the provision of an adjustment mechanism, such as a pulse width modulator, a variable resistor, or the like in an electrical circuit connecting the power source and the conductive element 228. Alternatively, or additionally, the adjustment mechanism includes a simple on/off switch in the circuit.

Further, the speed at which the magnetic element 224 oscillates can be adjusted by adjusting the frequency of the alternating currents. In some embodiments, a direct current can be applied to the conductive element 228 to offset the alternating currents so as to disassociate the heating of the elongate member 212, and thus, the vaporization of the vaporizable material therein, from the oscillation of the magnetic element 224. That is, the application of direct current could stop the oscillation of the magnetic element 224 while heating the elongate member 212.

While the vaporization chamber 210 can have a variety of configurations, the vaporization chamber 210, as shown in FIGS. 2A-2B, is defined by two opposing sidewalls 210a, 210b and a bottom wall 210c extending therebetween. The first sidewall 210a of the vaporization chamber 210 is also one of the sidewalls 202c of the first storage chamber 202, and the second sidewall 210b of the vaporization chamber 210 is also one of the sidewalls 202c of the second storage chamber 204. As such, in this illustrated embodiment, the vaporization chamber 210 is at least partially bounded by the first and second storage chambers 202, 204. As shown, the vaporization chamber 210 defines an airflow passageway 229 that extends therethrough.

The airflow passageway 220 is configured to direct air, illustrated as dash-lined arrow 230, through the vaporization chamber 210 so that the air 230 will mix with the vaporized material to form an aerosol, illustrated as dash-lined arrow 231. The airflow passageway 229 further directs the aerosol 231 through an outlet 211 of the vaporization chamber 210, and thus a mouthpiece 232 coupled to the vaporizer cartridge 200, for inhalation by a user. While a mouthpiece 232 is shown in FIGS. 2A-2B, a person skilled in the art will appreciate that in other embodiments, the mouthpiece 232 can be omitted and the user can directly puff on the cartridge 200 at an outlet (such as outlet 211 of vaporization chamber 210).

In some embodiments, at least one wall of the vaporization chamber 210, such as sidewall 210a and/or sidewall 210b, can be formed of, or coated with, a hydrophobic material so as to prevent any condensation from accumulating within the vaporization chamber 210. As such, any water that may be present in the aerosol 231 and in the air 230 can be carried through and out of the vaporization chamber 210 as the user puffs on the mouthpiece 232.

The air 230 enters the vaporization chamber 210 through the bottom wall 210c as a user puffs the mouthpiece 232. As such, the bottom wall 210c is configured to allow air 230 to readily pass therethrough and into the vaporization chamber 210. While the bottom wall 210c can have a variety of configurations, the bottom wall 210c is perforated, as shown in FIGS. 2A-2B. The perforations can be of any suitable size that allows air to pass through the bottom wall 210c. In certain embodiments, the size of the perforations can substantially prevent any vaporizable material dispensed from the first or second storage chambers 202, 204 or aerosol 231 to pass through the bottom wall 210c, and therefore inhibit undesirable leakage into other portions of a vaporizer body, such as vaporizer body 110 shown in FIGS. 1A-1D, coupled to the vaporizer cartridge 200. The bottom wall 210c can include any suitable number of perforations, and therefore the number of perforations is not limited by what is illustrated in the FIGS. 2A-2B. Alternatively or in addition, the bottom wall 210c can be formed of an air permeable material. Thus, the bottom wall 210c functions as an air inlet for the vaporization chamber 210.

The bottom wall 210c can also be configured to prevent air 230 and/or aerosol 231 within the vaporization chamber 210 from passing therethrough. That is, the bottom wall 210c can be configured as a one-way valve, and therefore only allow air 230 to pass through and into the vaporization chamber 210. In some embodiments, any of the remaining walls of the vaporization chamber 210 can be perforated and/or formed of an air permeable material to allow air to pass into (or out of) the vaporization chamber 210 as desired.

Terminology

For purposes of describing and defining the present teachings, it is noted that unless indicated otherwise, the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present.

Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments and implementations only and is not intended to be limiting. For example, as used herein, the singular forms "a," "an," and "the" are intended to include the plural forms as well, unless the context clearly indicates otherwise.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

Spatially relative terms, such as "forward", "rearward", "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings provided herein.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the teachings herein. For example, the order in which various described method steps are performed may often be changed in alternative embodiments, and in other alternative embodiments, one or more method steps may be skipped altogether. Optional features of various device and system embodiments may be included in some embodiments and not in others. Therefore, the foregoing description is provided primarily for exemplary purposes and should not be interpreted to limit the scope of the claims.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description. Use of the term "based on," herein and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail herein, other modifications or additions are possible. In particular, further features and/or variations can be provided in addition to those set forth herein. For example, the implementations described herein can be directed to various combinations and subcombinations of the disclosed features and/or combinations and subcombinations of several further features disclosed herein. In addition, the logic flows depicted in the accompanying figures and/or described herein do not necessarily require the particular order shown, or sequential order, to achieve desirable results. Other implementations may be within the scope of the following claims.

What is claimed is:

1. A cartridge for a vaporizer device, the cartridge comprising:
   a first storage chamber and a second storage chamber, the first storage chamber being configured to hold a first fraction of a vaporizable material and the second storage chamber being configured to hold a second fraction of the vaporizable material;
   an elongate member that is in fluid communication with the first storage chamber and the second storage chamber, the elongate member having a channel extending therethrough, the elongate member being configured to receive the vaporizable material; and
   a magnetic element disposed within the channel of the elongate member, the magnetic element being configured to selectively oscillate between a first position and a second position so as to substantially control the flow of the vaporizable material into the elongate member.

2. The cartridge of claim 1, further comprising a conductive element in selective communication with the magnetic element, the conductive element configured to substantially vaporize the vaporizable material within the elongate member to a vaporized material in response to receiving at least one electric current.

3. The cartridge of claim 2, wherein the conductive element is configured to produce an alternating magnetic field.

4. The cartridge of claim 2, wherein the at least one electric current includes a first electric current having a first polarity and a second electric current having a second polarity.

5. The cartridge of claim 2, wherein the conductive element is a coil that is substantially wound about at least a portion of the elongate member.

6. The cartridge of claim 1, wherein a portion of the first fraction of the vaporizable material flows into the elongate member when the magnetic element is in the second position.

7. The cartridge of claim 1, further comprising an inlet valve positioned at a first end of the elongate member, the inlet valve configured to substantially prevent backflow of the portion of the first fraction of the vaporizable material from the elongate member and into the first storage chamber.

8. The cartridge of claim 1, wherein a portion of the second fraction of the vaporizable material flows into the elongate member when the magnetic element is in the first position.

9. The cartridge of claim 1, further comprising an inlet valve positioned at a second end of the elongate member, the inlet valve configured to substantially prevent backflow of the portion of the second fraction of the vaporizable material from the elongate member and into the second storage chamber.

10. The cartridge of claim 1, wherein the magnetic element is a permanent magnet.

11. The cartridge of claim 1, further comprising a vaporization chamber that defines an airflow passageway that extends therethrough, and wherein the airflow passageway is configured to allow the vaporized material to combine with an influx of air such that the vaporized material passes out of the vaporization chamber.

12. A vaporizer device, comprising:
    a vaporizer body; and
    a cartridge that is selectively coupled to and removable from the vaporizer body, the cartridge including:
       a first storage chamber and a second storage chamber, the first storage chamber being configured to hold a first fraction of a vaporizable material and the second storage chamber being configured to hold a second fraction of the vaporizable material,
       an elongate member that is in fluid communication with the first storage chamber and the second storage chamber, the elongate member having a channel extending therethrough, the elongate member being configured to receive the vaporizable material, and
       a magnetic element disposed within the channel of the elongate member, the magnetic element being configured to selectively oscillate between a first position and a second position so as to substantially control the flow of the vaporizable material into the elongate member.

13. The device of claim 12, wherein the cartridge includes a conductive element in selective communication with the magnetic element, the conductive element configured to substantially vaporize the vaporizable material within the elongate member to a vaporized material in response to receiving at least one electric current.

14. The device of claim 13, wherein the conductive element is configured to produce an alternating magnetic field.

15. The device of claim 13, wherein the at least one electric current includes a first electric current having a first polarity and a second electric current having a second polarity that is opposite the first polarity.

16. The device of claim 12, wherein a portion of the first fraction of the vaporizable material flows into the elongate member when the magnetic element is in the second position.

17. The device of claim 16, wherein the cartridge includes an inlet valve positioned at a first end of the elongate member, the inlet valve configured to substantially prevent backflow of the portion of the first fraction of the vaporizable material from the elongate member and into the first storage chamber.

18. The device of claim 12, wherein a portion of the second fraction of the vaporizable material flows into the elongate member when the magnetic element is in the first position.

19. The device of claim 18, wherein the cartridge includes an inlet valve positioned at a second end of the elongate member, the inlet valve configured to substantially prevent backflow of the portion of the second fraction of the vaporizable material from the elongate member and into the second storage chamber.

20. A cartridge for a vaporizer device, the cartridge comprising:
    a first storage chamber and a second storage chamber, the first storage chamber being configured to hold a first fraction of a vaporizable material and the second storage chamber being configured to hold a second fraction of the vaporizable material; and
    a magnetic element disposed within an elongate member in fluid communication with the first and second storage members, the magnetic element configured to selectively oscillate between a first position and a second position so as to substantially control the flow of the vaporizable material into the elongate member.

* * * * *